United States Patent [19]

Kelly

[11] Patent Number: 5,496,257
[45] Date of Patent: Mar. 5, 1996

[54] APPARATUS FOR ASSISTING IN THE APPLICATION OF CARDIOPULMONARY RESUSCITATION

[75] Inventor: Kenneth B. Kelly, Belle Mead, N.J.

[73] Assignee: Kelly Medical Products, Inc., Princeton, N.J.

[21] Appl. No.: 231,334

[22] Filed: Apr. 22, 1994

[51] Int. Cl.$^6$ .................................................. A61H 31/00
[52] U.S. Cl. ............................... 601/41; 601/1; 601/134; 128/661.08
[58] Field of Search ................................. 601/1, 41, 42, 601/44, 97, 134, 135; 434/265, 262; 128/661.08, 640, 677

[56] References Cited

U.S. PATENT DOCUMENTS

| | | | |
|---|---|---|---|
| 3,760,794 | 9/1973 | Basham | 601/41 |
| 4,019,501 | 4/1977 | Harris. | |
| 4,077,400 | 3/1978 | Harrigan. | |
| 4,095,590 | 6/1978 | Harrigan. | |
| 4,166,458 | 9/1979 | Harrigan. | |
| 4,196,725 | 4/1980 | Gunderson. | |
| 4,237,872 | 12/1980 | Harrigan. | |
| 4,355,634 | 10/1982 | Kanter | 601/41 |
| 4,554,910 | 11/1985 | Lally. | |
| 4,588,383 | 5/1986 | Parker et al. | 601/41 |
| 4,733,670 | 3/1988 | Hays et al. | 128/640 |
| 4,863,385 | 9/1989 | Pierce. | |
| 4,915,095 | 5/1990 | Chun. | |
| 5,042,496 | 8/1991 | Sjonell | 128/677 |
| 5,230,342 | 7/1993 | Bobo, Jr. et al. | 128/677 |

*Primary Examiner*—Richard J. Apley
*Assistant Examiner*—Jeanne M. Clark
*Attorney, Agent, or Firm*—Plevy & Associates

[57] ABSTRACT

A portable apparatus for assisting a rescuer to administer cardiopulmonary resuscitation (C.P.R.) on a patient, having a housing that rests on the patient's chest so that chest compression forces are applied through the apparatus. The apparatus monitors compression force, the rate of compressions, and blood flow and actively provides this information to the rescuer so that the rescuer can be assured that C.P.R. is being properly administered.

14 Claims, 6 Drawing Sheets

APPARATUS FOR ASSISTING IN THE APPLICATION OF CARDIOPULMONARY RESUSCITATION

FIELD OF THE INVENTION

The present invention relates to devices that assist a person in administering cardiopulmonary resuscitation. More particularly, the present invention relates to portable devices that are placed on a patient's chest and both instruct the rescuer in how to optimally administer cardiopulmonary resuscitation and monitor the effectiveness of the cardiopulmonary resuscitation on the patient.

BACKGROUND OF THE INVENTION

When a person's heart stops beating on its own, blood circulation sufficient to maintain life can be obtained by periodically compressing the heart through a physical force being applied to the chest. Such methods of compressing the chest to create blood flow through the heart is an essential part of cardiopulmonary resuscitation (C.P.R.). The proper application of force applied to a person's chest and the rate of compression/decompression are largely governed by the physical characteristics of the person receiving C.P.R. For instance, the force used to compress the chest of a small child differs greatly from the force used to compress the chest of a large adult. If the amount of force used in administering C.P.R. is insufficient to properly compress the heart, the patient's blood flow would be inadequate and the patient may suffer brain damage or may fail to be resuscitated. Alternatively, if too much force is applied to a patient's chest, the patient may suffer significant injury such as injury to vital organs, broken ribs and/or internal bleeding.

The administration of C.P.R. also requires mouth-to-mouth resuscitation to be used in addition to cardiac compression. Mouth-to-mouth resuscitation fills the lungs with air and provides oxygen to the blood, while the cardiac compression circulates the newly oxygenated blood throughout the body. During ideal circumstances, C.P.R. is administered by two people. One person performs the repeated cardiac compression while the other person periodically performs the needed mouth-to-mouth resuscitation and monitors the vital signs of the patent. The problem with administering emergency C.P.R. is that circumstances are typically far from ideal. In a situation, such as an accident or a heart attack, C.P.R. is often administered by a single person in an environment of confusion and near panic. In this confusing environment, the person administering C.P.R. must remember how and where to perform chest compression, how hard to compress the chest for any given patient, how many times per minute to perform the chest compressions and how often to stop the chest compressions in order to administer mouth-to-mouth resuscitation. All of this information is hard to remember for even professional rescue workers, however, it is much more difficult to remember by a bystander that may have only had C.P.R. training once or twice in his or her life.

The prior art is replete with devices that can be used to help teach and/or administer C.P.R. to a patient. Many such prior art devices take away much of the guess work involved in administering C.P.R. by prompting the person administering C.P.R. to take various actions at the appropriate times. Examples of such prior art references are as follows.

U.S. Pat. No. 4,863,385 to Pierce, entitled CARDIOPULMONARY RESUSCITATION SEQUENCER and issued Sep. 5, 1989, shows a compact portable computer for assisting in the application of C.P.R. The Pierce device has variable inputs that allows a person to input the physical size of the patent. The Pierce device then visually and audibly informs a person as to when to apply cardiac compression and when to administer mouth-to-mouth resuscitation.

U.S. Pat. No. 4,077,400 to Harrigan, and its progeny U.S. Pat. Nos. 4,095,590; 4,166,458; and 4,237,872 all entitled EXTERNAL CARDIAC RESUSCITATION AID all show devices that are placed on a patient's chest that assist in the administration of C.P.R. The disclosures of these Harrigan patents disclose the use of pressure gauges, and various audio and visual indicators that help instruct a person in how to properly administer C.P.R. These patents also show the use of an external blood pressure mounting device such as a cuff or wrapping that is wrapped around an extremity of the patient receiving C.P.R.

The purpose of C.P.R. is to artificially cause oxygenated blood to flow through the body when the heart and lungs stop working on their own. However, even if C.P.R. is administered in a textbook fashion, there is no guarantee that enough blood will flow through the body to maintain life in the patient. As has been previously explained, C.P.R. is often administered by a single undertrained person in a highly stress-filled and confusing environment. In such an environment, the person administering C.P.R. cannot stop to check blood flow in the patient. This is because the blood only flows during C.P.R. and stops when the C.P.R. stops. As such, a single person can only assume that he or she is properly administering C.P.R. since a single person cannot administer C.P.R. and check blood flow at the same time.

A need exists in the art for a device that helps a person administer C.P.R., wherein the device provides a dynamic readout of the patient's blood flow rate during the administration of C.P.R. By producing a dynamic display of a patient's blood flow rate, the person administering the C.P.R. can see if the C.P.R. is working on the patient. As a result, the person administering the C.P.R. can make adjustments, such as pushing harder or more frequently than normal to optimize the blood flow rate in that particular patient.

It is therefore an object of the present invention to provide an improved device that assists in the administration of C.P.R. by visually and audibly prompting a person to optimally perform C.P.R.

It is yet another object of the present invention to provide such a device with dynamic display that shows blood flow rate, thereby allowing the person administering C.P.R. to adjust his/her technique to optimize blood flow.

SUMMARY OF THE INVENTION

The present invention is a portable device that assists a rescuer in administering cardiopulmonary resuscitation (CPR) to a patient by helping eliminate some of the guess work that accompanies the administration of C.P.R. The present invention device includes a housing that is placed on a patient's chest. The housing includes at least one surface adapted to receive a manually applied chest compression force administered by the rescuer. A cushioned pad extends from the housing and rests upon the patient's chest. As a result, the manually applied compression force is equally distributed across the area of the cushioned pad, thereby minimizing trauma to the patient. A pressure sensor is disposed within the cushioned pad. As a result, the pressure being applied to a patient during C.P.R. is measured and displayed on a gauge. This display enables the rescuer to determine whether the chest compression force being applied is adequate for the size and conditions of the patient. Audible and visual indicator are also disposed on the housing. The audio and visual indicators provide signals to the rescuer informing the rescuer as to the proper compression rate per minute, and the proper times to administer mouth-to-mouth resuscitation. The audio and visual indicators are also used to warn the rescuer if C.P.R. is being administered in a wrongful or ineffective manner. For instance, the audio and visual indicators may produce specific warning signals should the chest compression force be too hard or too soft or if the chest compression rate is too fast or too slow.

In a preferred embodiment of the present invention, a disposable blood flow sensor may be joined to the housing. The blood flow sensor attaches to the patient and measures blood flow within the patient during C.P.R. A display shows the amount of blood flow measured by the blood flow sensor. This allows the rescuer to read the blood flow while he/she is administering C.P.R. As a result, the C.P.R. technique can be actively modified if it is seen that the blood flow rate is too low.

BRIEF DESCRIPTION OF THE FIGURES

For a better understanding of the present invention, reference may be had to the following description of an exemplary embodiment thereof, considered in conjunction with the accompanying drawings, in which:

FIG. 1b is a side view of the embodiment shown in FIG. 1a;

DETAILED DESCRIPTION OF THE INVENTION

Figure 1A:
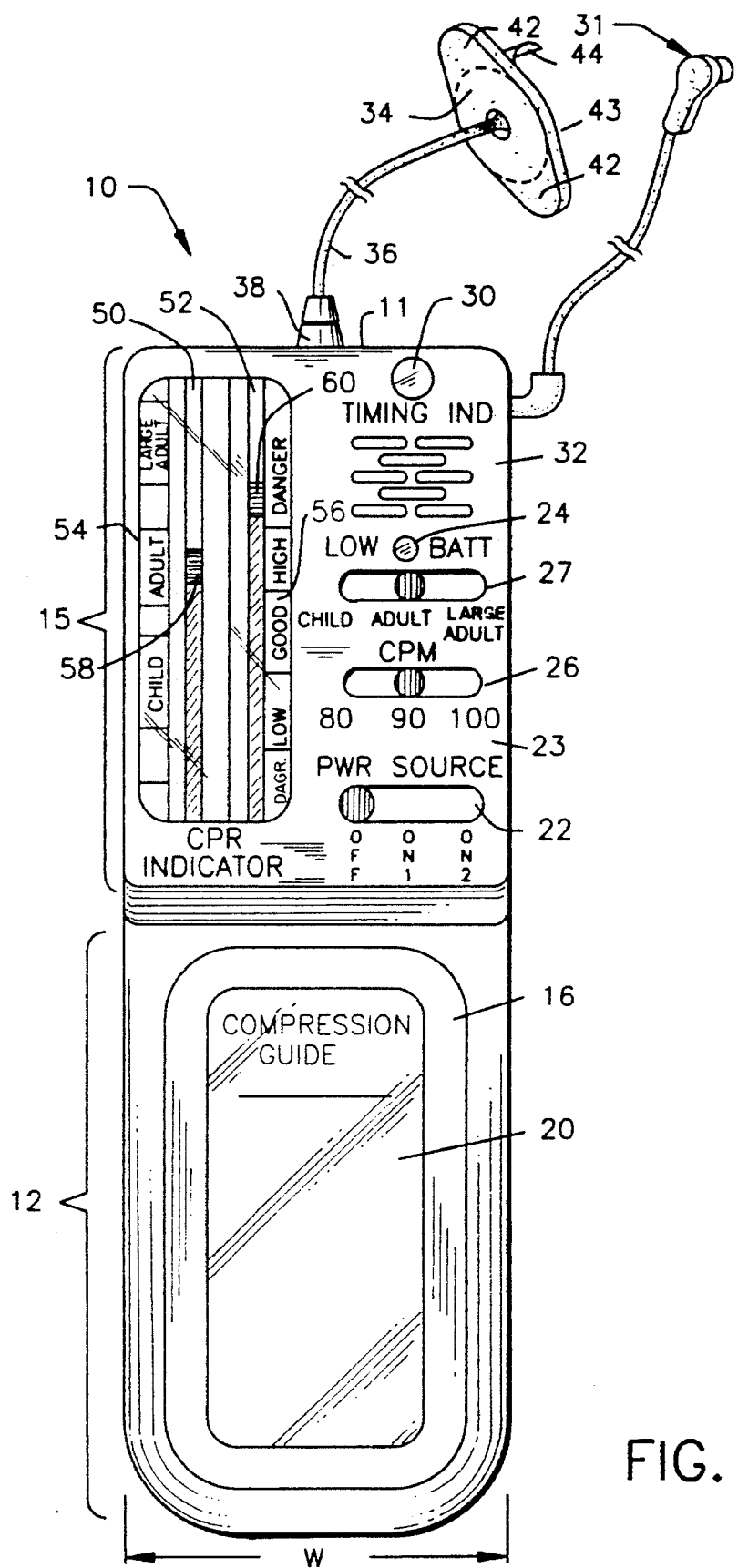
FIG. 1a is a front plan view of one preferred embodiment of the present invention.
Figure 1B:
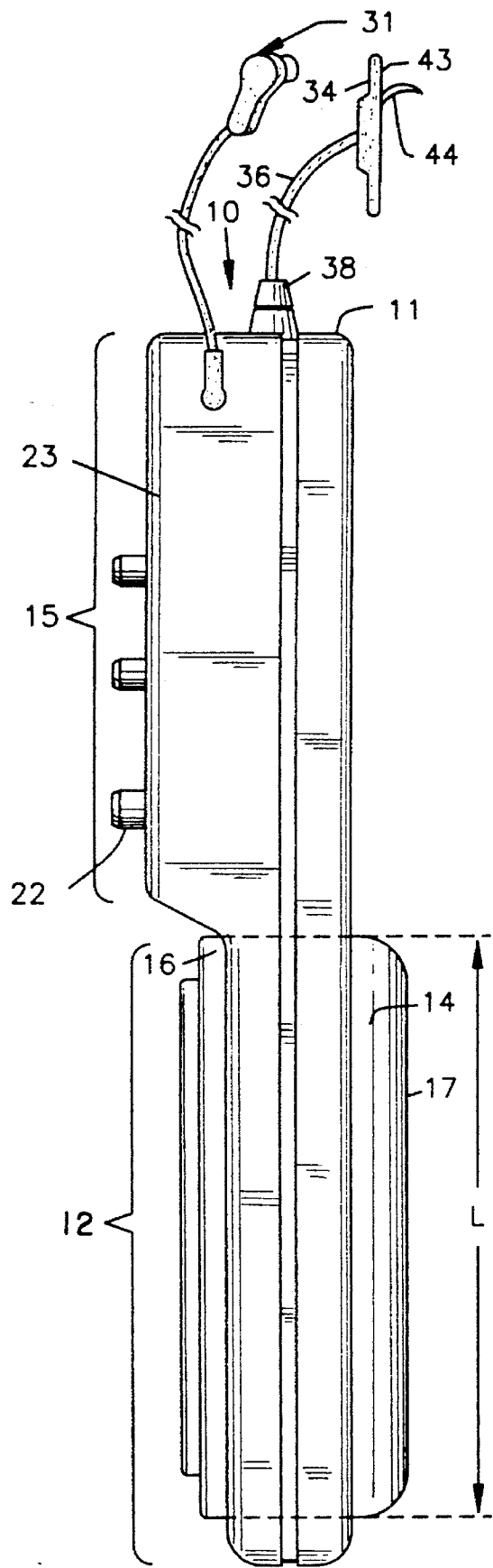

Referring to FIGS. 1a and 1b, an exemplary embodiment of the present invention apparatus 10 is shown. The present invention apparatus 10 is a light weight, transportable device that is placed on the chest of a person who requires cardiopulmonary resuscitation (C.P.R). The purpose of the apparatus is to provided the person administering C.P.R. with visual and audible signals that inform a person when to perform certain aspects of C.P.R. and to inform the person as to whether or not the C.P.R. technique being used is effective.

In the embodiment shown, the present invention apparatus 10 includes a housing 11 divided into a compression region 12 and an control panel region 15. A compression pad 14 extends downwardly from the compression region 12 and is the part of the apparatus 10 that actually contacts the body of the person receiving C.P.R. In a preferred embodiment, the compression pad 14 is a cushioned member that conform to the contours of a patient's chest as the compression pad 14 is pressed against the patient's chest. By having a compression pad 14 that is cushioned, the forces applied to the compression region 12 are more evenly distributed onto the patient. As a result, there is less of a chance that the force being applied to the patient will cause internal injuries or external bruising. A flat, stiff surface 16 is disposed within the compression region 12 directly above the compression pad 14. It is upon the flat surface 16 that a person administering C.P.R. places his or her hands during chest compression (see FIG. 3). As can be ascertained, by applying a force to the flat surface 16, the force is transferred to a patient's chest via the compression pad 14. Since the flat surface 16 is relatively stiff, any force applied to the flat surface 16 will be evenly distributed across the compression pad 14 and onto the patient.

It will be understood that the embodiment shown in FIGS. 1a and 1b is merely exemplary and other features may be added to the shown apparatus 10 to improve its performance. For instance, an adhesive element (not shown) such as double sided tape or a spray-on adhesive may be applied to the surface 17 of the compression pad 14 that actually contacts the patient. The adhesive element would then hold the compression pad 14 in one set position on the patent's chest, thereby preventing the overall apparatus 10 from moving during the administration of C.P.R. Similarly, the bottom surface 17 of the compression pad 14 may be textured to increase the coefficient of friction associated with that surface. This also helps prevent the compression pad 14 from moving during the administration of C.P.R.

In the shown embodiment, the person administering C.P.R. places his/her hands on the flat surface 16. This surface may become slick. Accordingly, the flat surface 16 may be textured in a manner that increases its coefficient of friction. This helps prevent a persons hands from slipping off of the flat surface 16 during the administration of C.P.R. In an alternate embodiment, the flat surface 16 may be replaced with a contoured element (not shown) that is shaped to match the contours of a person's hand. As such, when a person places his/her hand onto the contoured element, it fits securely into one predetermined orientation. In an alternate modification, a soft material or gel pack (not shown) may be substituted for the flat surface 16. The soft material would deform under the pressure of a person's hand and conform to the contours of the hand. Consequently, a person's hand would settle into the soft material and would become securely fitted into one set orientation. As such, the surface a rescuer places his/her hands on would be very similar to the cushioned compression pad 14 that rests upon the patient.

The prior art is replete with cushioned compressive pads that are used in conjunction with C.P.R. devices. However, such prior art compressive pads are typically filled with either air or liquid. The problem with such air or liquid filled pads is that they are easily damaged. If a small hole develops in the pad, the compression pad is destroyed and the C.P.R. device is rendered useless. Additionally, liquid filled compression pads are heavy, making the C.P.R. device much heavier than it need be. Furthermore, the use of air filled or liquid filled compression pads lends itself to mechanical pneumatic or hydraulic gauges. Such gauges are typically cumbersome and heavy and commonly only have an accuracy of plus or minus a few pounds per square inch. In the preferred embodiment of the present invention apparatus 10, a cushioned compressive pad 14 is used that is neither liquid filled nor air filled, but rather includes a light weight electronic pressure sensor. Buy utilizing the electronic pressure sensor, very accurate pressure measurements can be obtained at a comparatively low cost that are not available through pneumatic or hydraulic gauges in the same price range. Similarly, pressure measurements can be obtained at a much reduced weight and with a much higher degree of durability and impact resistance. The technology of providing a low cost, highly accurate electronic pressure sensor disposed within a cushioned member is shown by U.S. Pat. No. 4,987,783 to D'Antonio entitled SENSOR AND TRANSDUCER APPARATUS, which is incorporated herein by reference.

In FIGS. 1a and 1b, the compression pad 14 is shown to be practically as large as the entire compression region 12 and is larger than the flat surface 16. The flat surface 16 is sized so that an adult can comfortably place his or her hands on the flat surface 16 and administer cardiac compressions (see FIG. 3). A compression pad 14 of the shown size is appropriate for adult patients and most children over the weight of sixty pounds. However, for use on an infant or a small child, such a compression pad size is entirely inadequate. As such, it will be understood that the present invention device can be made with a much smaller pad than is shown. For adults the compression pad 14 may have a width W of between 1½ to 3 ½ inches and a length L of between 3 inches and 6 inches. However, for infants and small children, the compression pad 14 should have a width W between ½ inch and 1 inch and a length L of between 1 inch and 2 inches. The size of the flat surface 16 also depends upon whether the overall apparatus 10 is designed for use on an adult or on an infant. In the case of an adult, the flat surface 16 should be large enough to enable an adult rescuer to place two clasped hands upon its surface. In the case of an infant, the flat surface 16 could be much smaller since C.P.R. is typically applied with only two fingers.

An instruction guide 20 is disposed on the flat surface 16 facing upwardly. The instruction guide 20 contains graphics and text that show how to place the apparatus 10 on a patients chest, and provide a brief overview of how to use the present invention apparatus 10 in administering C.P.R.

An on/off switch 22 and low batter indicator 24 are present on the face surface 23 of the control panel region 15. The present invention apparatus 10 is transportable and is therefore preferably powered by battery. In the preferred embodiment, the apparatus 10 contains at least two batteries (not shown) each being part of a separate power circuit. C.P.R. often has to be administered for prolonged periods, i.e. 10–45 minutes, while a patient is being transferred to a medical facility. Since the present invention apparatus 10 instructs a person in how to optimally administer C.P.R. it is very important that the apparatus not fail during the administration of C.P.R. The on/off switch 22 has three settings, namely "OFF", "ON1" and "ON2". The "OFF" setting disables the apparatus 10 by uncoupling the batteries to the remaining circuitry. The "ON1" setting couples a first battery, or set of batteries, to the remaining circuitry, thereby enabling the device. Should the first battery become weak, the low battery indicator 24 will light providing a visual indication as to the deficient condition of the first battery. The person administering C.P.R., upon seeing the low batter indicator 24, may then move the on/off switch 22 to the "ON2" position. This couples the circuitry of the apparatus 10 to a new, fully charged second battery or set of batteries, thereby effectively doubling the operational time for the apparatus 10. The use of additional switch positions and corresponding additional batteries may also be used. However, at least two battery circuits are preferred to add a desired safety factor to the electrical operation of the present invention apparatus 10.

In FIG. 1a, a compression rate per minute (C.P.M.) switch 26 is provided on the face surface 23 of the control panel above the on/off switch 22. The C.P.M. switch 26, as shown, has settings corresponding to three different rates. The rates shown are 80 C.P.M., 90 C.P.M. and 100 C.P.M. however many other choices between 55 C.P.M. and 120 C.P.M. may be incorporated. As will later be explained, during use, the rescuer sets the C.P.M. switch 26 at a desired rate. If the rescuer wants to change the rate, the C.P.M. switch is changed to a new desired setting.

An optional patient type switch 27 may be present on the face surface 23 of the control panel region 15. In the shown embodiment, the patient type switch 27 has three settings, one for children, one for small adults and one for large adults. During use, the patient type switch 27 is set to the estimated size of the person to receive C.P.R. To properly administer C.P.R., the number of chest compressions per minute (CPMs) and the compression force to be applied to optimize blood flow is dependent partially upon the size of the person receiving C.P.R. As will later be explained, by setting the patient type switch 27 to the proper size classification, the proper compression force for a patient can be read into the apparatus from a stored memory. For example, a person weighing 200 pounds may require a chest compression force of ninety (90) pounds per square inch. However, such a force may be highly dangerous to a 100 pound person who requires a compression force of fifty five (55) pounds per square inch. The proper compression force value, for a selected size class, may be electronically stored within the circuitry of the apparatus 10. As will be later explained, the apparatus 10 may include a ROM memory circuit that contains the needed information for the various weight classes.

At least one visual indicator 30 and audible indicator 32 are present on the face surface 23 of the control panel region 14. As will be explained, the visual indicator 30 and audible indicator 32 are coupled to a control circuit governed by the C.P.M. switch 26. The primary function of the visual indicator 30 and audible indicator 32 is to pace the person administering C.P.R. in the proper compression rate per minute for a given sized patient. For example, the visual indicator 30 may flash and the audible indicator 32 may sound a tone each time within a minute cycle that a chest compression force should be administered, thereby instructing the person administering C.P.R. to the proper pace. The visual indicator 30 is preferably an incandescent bulb with a colored lens, such as green or red. However, the visual indicator 30 may also be a flash bulb or a similar strobe that emits a very short but intense flash of light. The use of a flash will produce a highly noticeable visual indication that can be readily observed by the person administering C.P.R. in a confused and chaotic environment.

In the preferred embodiment, the audible indicator 32 emits a tone that corresponds in length to the proper compression phase used during C.P.R. In other words, a tone is given that informs the rescuer of how long he/she should apply a compression force to the patient's chest. The audible indicator 32 therein provides a second tone that serves as a warning should the rescuer not completely release pressure from the chest cavity during the relaxation phase of C.P.R. in between compressive cycles or if the compression force is released prematurely.

The audible indicator 32 may be a simple piezoresistive buzzer. However, as will be explained, the audible indicator 32 may be a speaker coupled to a voice synthesizer. As such, audible commands such as "start", "stop", "push", "faster", "slower" may be electronically spoken to the person administering the C.P.R. Both the audible indicator 32 and the visual indicator 30 may also be used to sound various alarms, should C.P.R. be administered in a wrongful or ineffective manner.

An optional earphone 31 may be attachable to the apparatus 10. The earphone 31 provides the same audible signals as does the audible indicator 32. The optional earphone 31 may be worn by the rescuer directly in his/her ear, whereby the rescuer will be able to clearly hear the various audible signals despite the level surrounding noise.

A disposable blood flow sensor 34 may be coupled to the present invention apparatus 10. The blood flow sensor 34 may utilize any known blood flow sensing technology but is preferably an ultrasonic transducer. Blood flow sensors that utilize ultrasonic transducers are well known in the art and need not be described herein. As will be later explained, the circuitry required to drive the blood flow sensor 34 and convert signals produced by the blood flow sensor 34 into actual blood flow values, are contained within the circuitry of the apparatus housing 11. The blood flow sensor 34, intercommunicates with circuitry within the apparatus housing 11 via a flexible connection conduit 36. A coupling 38 is disposed at the proximal end of the connection conduit 36, thereby allowing the connection conduit 36 to be easily connected or disconnected to the remainder of the apparatus 10. Such an intercoupling promotes the use of a disposable blood flow sensor 34 and connection conduit 36 that can be replaced each time the apparatus is used.

In the shown embodiment, the blood flow sensor 34 includes a set of flanges 42 that radially extend from the center of the blood flow sensor 34. The flanges 42 each have a surface 43 that lay in a common plane. Adhesive is applied to the common plane surface 43 so that the flanges 42 can be adhered to a patient's skin. A protective piece of paper 44 is placed over the adhesive before the blood flow sensor 34 is used. When needed, the protective paper 44 is removed and the blood flow sensor 34 is adhered to the body of the person receiving C.P.R. As will be later explained, the present invention apparatus 10 is placed on a person's chest with the blood flow sensor 34 extending toward the persons neck. As a result, the preferred position for placing the blood flow sensor 34 is on the patient's neck on top of the jugular vein and/or carotid artery. Accordingly, the length of the flexible connection conduit 36 should be long enough to facilitate the placement of the blood flow sensor 34 at this position. The positioning of the blood flow sensor 34 on the neck is also preferred because it directly measures blood flow to the brain. As is well known, the brain is one of the bodies most sensitive organs to oxygen deprivation. By directly monitoring blood flow to the brain, a person administering C.P.R. has the best chance of ensuring that the C.P.R. is performed in a manner that optimize blood flow to the brain.

Two gauges are present on the face surface 23 of the control panel region 14. The two gauges include a compression force gauge 50 and a blood flow gauge 52. The gauges 50, 52 may be mechanical in structure, however, both gauges 50, 52 may alternatively be part of a electronic display. In the later form, both gauges can be part of a liquid crystal display LCD, electrophoretic display or like electronic display. Despite the structure of the gauges, each gauge 50, 52 includes indicia of scale 54, 56 and a gauge indicator 58, 60 that moves in relation to the indicia of scale 54, 56. The indicia of scale 54, 56 for either the compression force gauge 50 or the blood flow gauge 52 may be numerical values, text or may be a color coded scale having a green zone, indicative of acceptable values, and red zones indicative of unacceptable values. If an electronic display is used, the indicia of scale 54, 56 may be electronically produced images, as would be the gauge indicators 58, 60. The relative movement of the gauge indicators 58, 60 would therefore be produced by recursively updating the electronic image.

Figure 2:
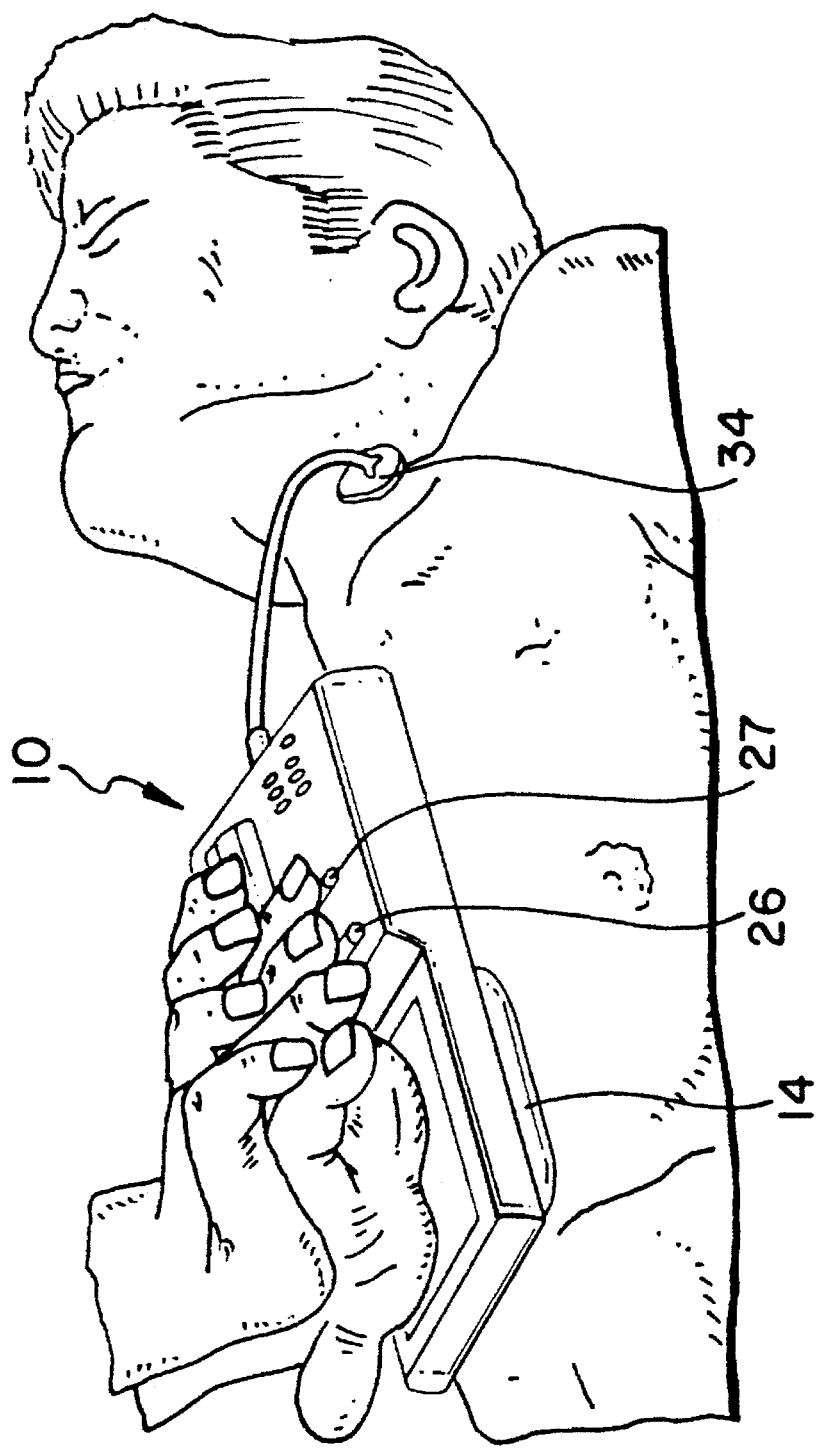
FIG. 2 is a perspective view of the embodiment of FIG. 1, shown in use on a patient.
Figure 3:
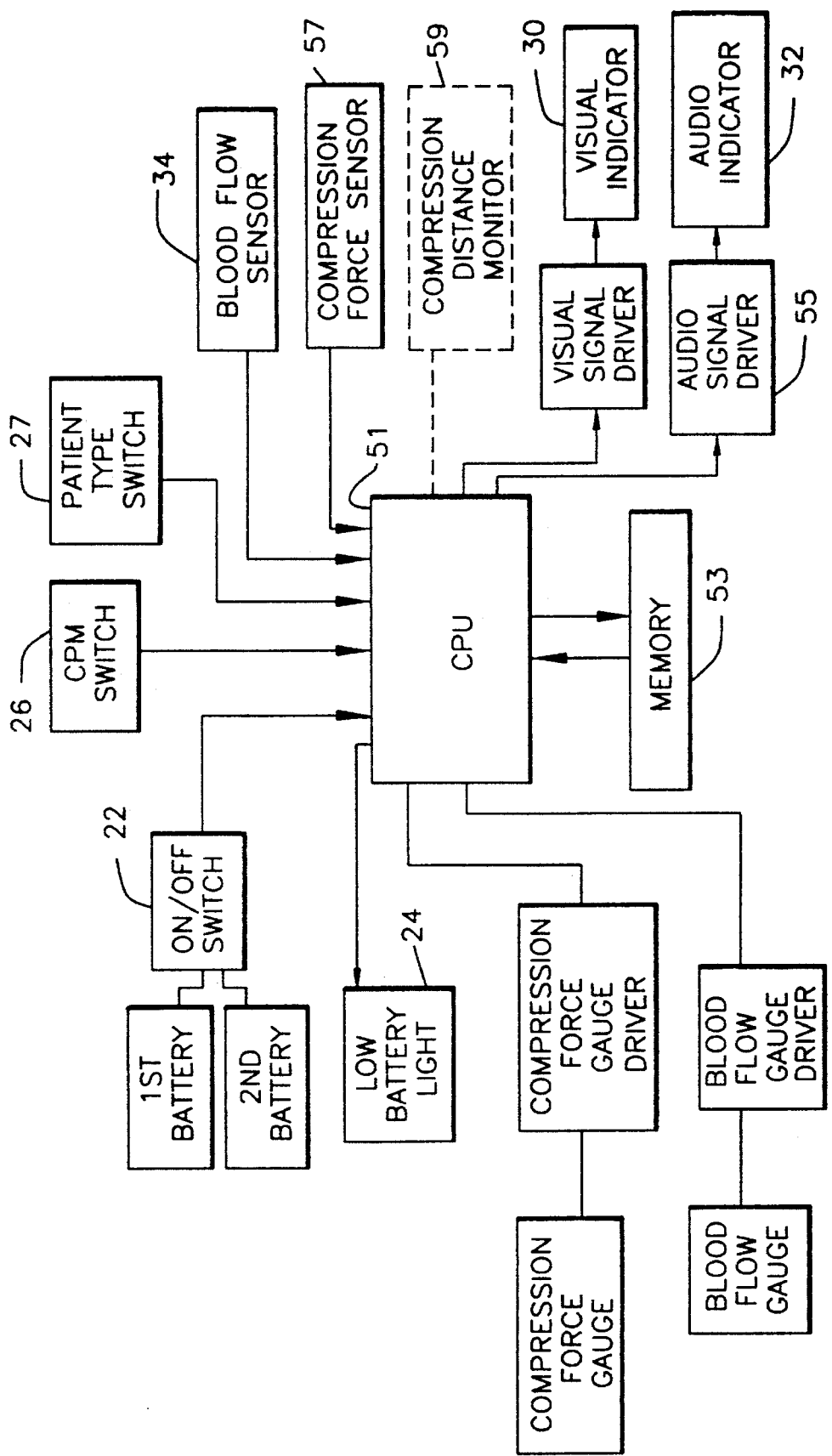
FIG. 3 is a block diagram schematic of the components of present invention.

Referring to FIG. 2, it can be seen that the present invention apparatus 10 is placed upon the chest of a person requiring C.P.R. in a position that orients the compression pad 14 just above the sternum on the chest. The blood flow sensor 34 is placed on the patient's neck. If the apparatus 10 includes a patient type switch 27, the apparatus 10 can be calibrated to the size of the patient by selecting the appropriate patient type (i.e. child, small adult, large adult). Similarly, the desired C.P.M. rate can be selected by manipulating the C.P.M. switch 26. Current standards are 80 to 100 C.P.M. depending upon patient type. With the apparatus enabled and properly initialized for the patient, the rescuer places his/her hands on the flat compression surface 16 and begins to administer chest compression forces as prompted by the apparatus. Referring to FIG. 3 it can be seen that within the present invention apparatus includes a central processing unit (C.P.U.) 51. The C.P.U. 51 may be coupled to a memory source 53 such as a ROM chip. The use of a memory is an optional feature of the present invention. In its simplest form, the apparatus 10 is enabled by manipulating the on/off switch 22. The apparatus 10 is then placed on a patient's chest. As will be explained in conjunction with FIG. 4, the C.P.U. 51 then drives the visual indicator 30 and the audible indicator 32 to prompt the rescuer into properly administering C.P.R. However, in alternate embodiments, the C.P.U. performs many additional functions in both prompting the rescuer in the various aspects of C.P.R. and monitoring the effectiveness of the C.P.R. being administered. If the C.P.U. 51 is performing monitoring functions, the C.P.U. 51 compares actual measured values to stored acceptable values, thus the C.P.U. 51 must have some memory capabilities.

Figure 4:
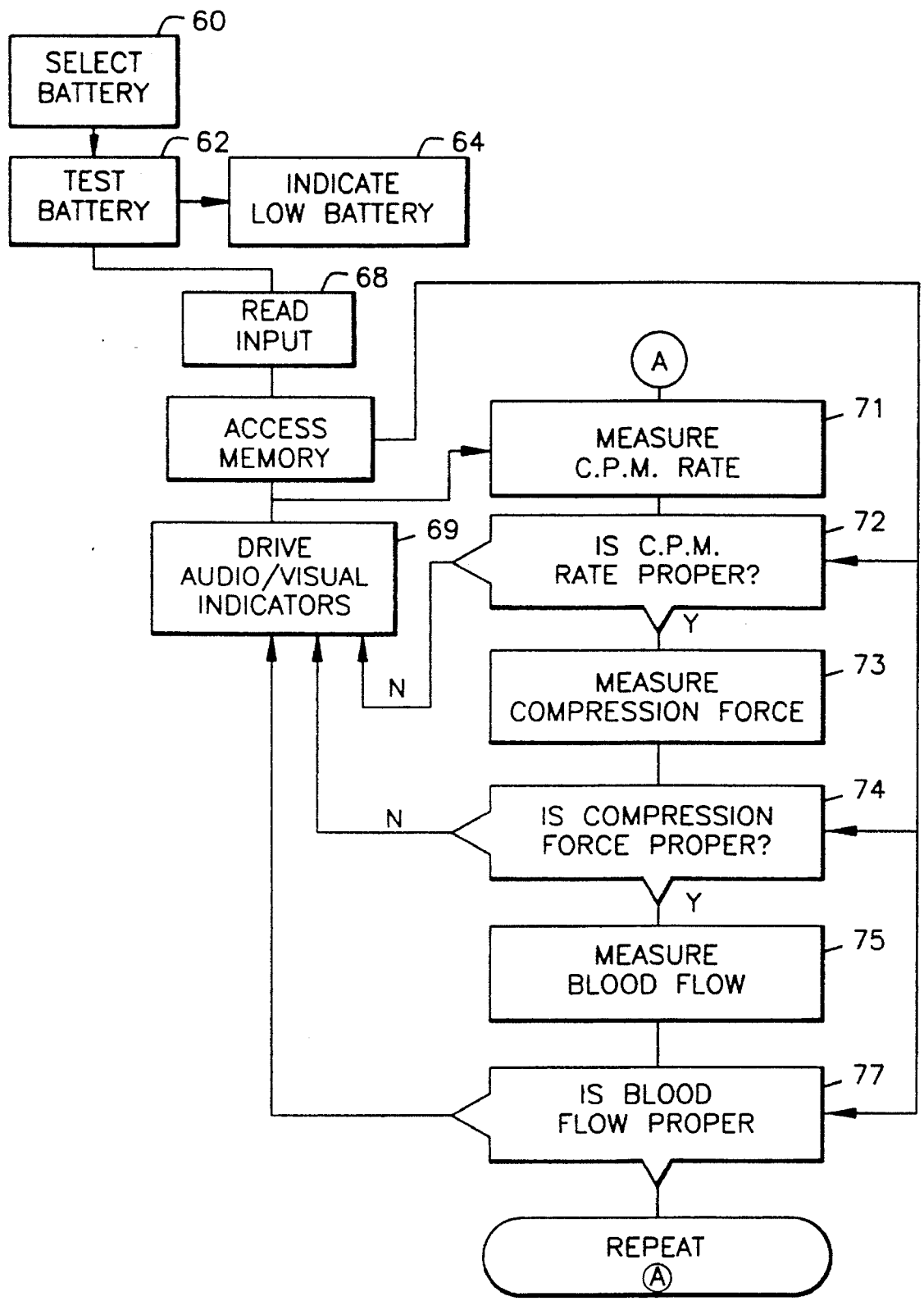
FIG. 4 is a flow diagram showing the method of operation of a preferred embodiment of the present invention.

Referring now to FIG. 4 in conjunction with FIG. 3, it can be ascertained that the present invention device 10 is activated by the manipulation of the on/off switch 22 and the selection of a battery source. This operation is indicated by box 60 in FIG. 4. Once activated, the power of the battery is recursively monitored. If the battery power falls below a predetermined level, the low batter indicator 24 lights. (See boxes 62 and 64.) The lighting of the low battery indicator 24 alerts the person administering C.P.R. to again manipulate the on/off switch 22 and change to the secondary battery source. The recursive testing of the battery source maybe performed by a dedicated circuit. However, the battery source testing may also be performed by the C.P.U. 51. In the previously shown embodiment, the on/off switch 22 has two settings for two different battery settings. The settings are selected by the tactile manipulation of the on/off switch 22. In an alternate embodiment, it should be understood that the switching between multiple battery sources could be an automated feature performed by the C.P.U. or a dedicated circuit. As a result, the present invention apparatus 10 may automatically change from one battery to another, if the first battery falls below a predetermined threshold power level.

Once the apparatus 10 is empowered, the person utilizing the apparatus to administer C.P.R. manipulates the C.P.M. switch 26 to reflect a desired rate of chest compressions. The C.P.U. 51 within the apparatus reads the value set by the C.P.M. switch 26. See box 68 of FIG. 4.

The C.P.U. 51 drives the visual indicator 30 and audible indicator 32. See box 69 in FIG. 4. In a preferred embodiment, the C.P.U. 51 flashes the visual indicator 30 each time a chest compression force should be administered. As a result, the visual indicator 30 flashes at the same rate as the selected compression rate per minute for the patient. Simultaneously, the audible indicator 32 provides audible signals corresponding to the required compression rate per minute. As a result, both an audible and a visual signal are provided that are indicative of the proper chest compression rate for the patient receiving C.P.R. The audible signals may also be sent through the earphone 31, if such an earphone 31 is used in conjunction with the present invention apparatus. The audible signal produced by the audible indicator 32 may be a monotone signal but may also be synthesized voice instruction. For example, the audible signal may be a synthesized voice that repeated states "push" each time a chest compression is to be administered. In such an environment, an audio signal driver 55 capable of producing synthesized speech would be driven by the C.P.U. 51. The C.P.U. 51 may also drive the audible indicator 32 and/or the visual indicator 30 to inform the person administering C.P.R. as to when chest compressions should be supplemented with mouth-to-mouth resuscitation. For example, two breaths of mouth-to-mouth resuscitation are given by a sole rescuer typically every fifteenth chest compression. As such, the audible indicator 32 and/or visual indicator 30 may provide signals to the rescuer every fifteenth compression to remind the rescuer to perform the required mouth-to-mouth resuscitation. The audible signal produced may also be either a specific tone or sequence of tones or may be a synthesized voice which states "mouth-to-mouth" or a similar audible instruction. Such audible and visual indications would remind the rescuer to perform mouth-to-mouth resuscitation at the proper times. In the preferred embodiment a tone is used. A tone is given at a rate corresponding to the selected chest compression rate. The duration of each tone corresponds to the length of the compression stroke. As such, the rescuer should push down on the patient's chest for the same length of time as the tone sounds. As a result, the present invention apparatus 10 may be set for a two men rescue team, whereby the appropriate audible and visual signals are provided at every fifth compression.

The rate at which a rescuer applies chest compressions is monitored by the C.P.U. 51. See box 71 in FIG. 4. The C.P.U. 51 counts the number of times a chest compression is administered by measuring the cyclical peak values of force detected by the compression force sensor 57 within the compression pad. The C.P.U. 51 compares the actual rate of chest compressions to the optimal compression rate set by C.P.M. switch 26. If the actual rate of chest compressions is too fast or too slow, the C.P.U. 51 provides a warning signal utilizing the audible indicator 32 and/or the visual indicator 30. See box 72 in FIG. 4. For instance, the C.P.U. 51 may cause the visual indicator 30 to flash in a given sequence or the audible indicator 32 may emit a given sequence of tones. Furthermore, the audible indicator 32 may emit a synthesize voice instruction such as "slower" or "faster" to inform the rescuer in how to improve his or her technique. Furthermore, if the rescuer does not compress the patient's chest for the proper duration of time in each compression stroke, the C.P.U. 51 sounds a warning signal utilizing the audible indicator 32 and/or the visual indicator 30.

If the present invention apparatus 10 includes a patient type switch 27, the C.P.U. 51 will also read the value set. With the patient type read by the C.P.U. 51, the C.P.U. 51 may retrieve operational data associated with the selected patient type from memory. The operational data retrieved would include a desired compression force and any other variables that are patient size related. If the present invention apparatus utilizes an electronic display for the compression force gauge 50 and blood flow gauge 52, (see FIG. 1a) the C.P.U. 51 may set up the indicia on the compression force gauge and the blood flow gauge to correspond to the operational requirements of a given weight class. For instance, if the patient size switch 27 is set at a patient type of a child, the compression force gauge would be initialized so that the average optimum compression force for that weight class is positioned at the center of the gauge. Similarly, the blood flow gauge would be initialized to position the blood flow rate in the center of that gauge. Similarly, if the compression force gauge and/or the blood flow gauge is color coded, perhaps having green zones and red zones, the C.P.U. 51 may initialize the various color coated regions to correspond to the weight classification of the patient.

In an alternate embodiment a compression distance monitor device 59 may be coupled to the C.P.U. 51, wherein the compression distance monitor 59 detects how far the patient's chest is compressed during a compression stroke. Optimally a rescuer wants to compress a patient's chest between 1.5 inches and 2.0 inches during the compression stroke. The compression distance monitor 59 informs the C.P.U. 51 of the distance the patient's chest is being compressed. If the patient's chest is not being compressed far enough the C.P.U. 51 may change the indicia on the compression force gauge 50 so that the rescuer presses harder. If an analog display is used, the C.P.U. 51 may sound a warning signal utilizing the audible indicator 32 and/or the visual indicator 30 to inform the rescuer to either press harder or easier on the patient's chest. As chest compressions are administered to a patient through the present invention apparatus 10, the peak pressure being applied is read by the C.P.U. 51. See box 73 in FIG. 4. The C.P.U. 51 then compares the actual pressure being applied to the desired pressure that should be applied. If the actual pressure being applied is too great or to small, the C.P.U. 51 may provide a warning signal utilizing the audible indicator 32 and/or the visual indicator 30. See box 74 in FIG. 4. For instance, the C.P.U. 51 may cause the visual indicator 30 to flash in a given sequence or the audible indicator 32 may emit a given sequence of tones. In place of such tones, the audible indicator 32 may emit a synthesized voice instruction such as "harder" or "softer" to inform the rescuer of the problem being encountered and the proper solution.

The blood flow sensor 34 is also coupled to the C.P.U. 51. As such, the C.P.U. 51 monitors the blood flow being measured by the blood flow sensor 34. See box 75 in FIG. 4. The C.P.U. 51 then compares the blood flow being measured to the desired range of blood flow retrieved from memory. If the actual blood flow being measured is too fast or too slow, the C.P.U. 51 provides a warning signal, again utilizing the audible indicator 32 and/or the visual indicator 30. See box 77 in FIG. 4. For instance, the C.P.U. 51 may cause the visual indicator 30 to flash in a given sequence and/or the audible indicator 32 may emit a given sequence of tones. Instead of tones, the audible indicator 32 may emit a synthesize voice instruction such as "push harder" to inform the rescuer that the blood flow is insufficient and the C.P.R. is not being properly administered. The C.P.U. 51 repeatedly monitors C.P.M. rate, compression force, and blood flow rate until C.P.R. is no longer being applied to the patient.

Figure 5:
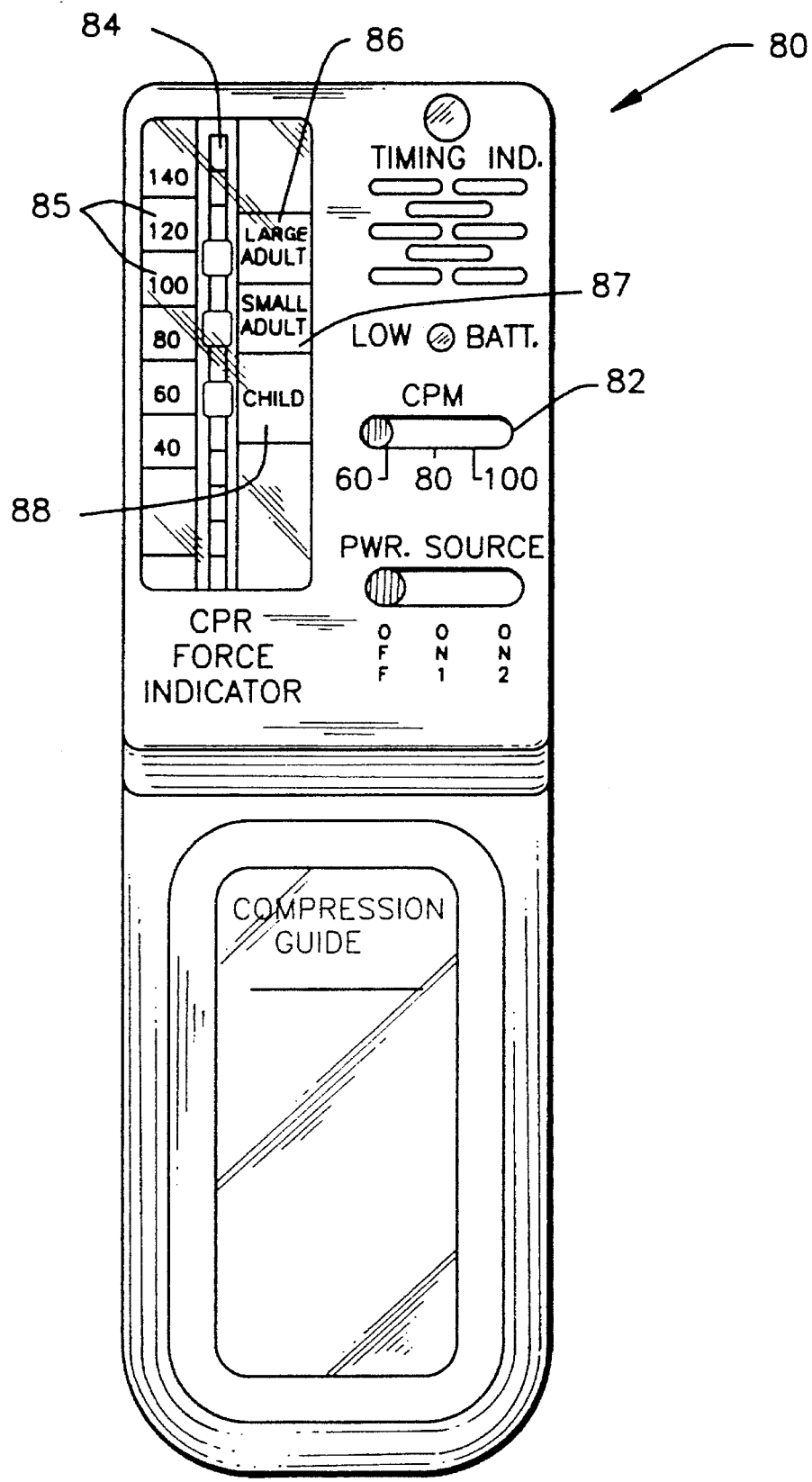
FIG. 5 is a front view of an alternate embodiment of the present invention.

Referring to FIG. 5, a second preferred embodiment of the present invention apparatus 80 is shown. In this embodiment, no blood flow sensor or gauge is present. Additionally, the patient size switch of the previous embodiment is not used and only the compression rate switch 82 is present. As a result, the lack of a blood flow sensor and the use of a manual compression rate switch eliminates the need for a complex stored memory and greatly reduces the complexity of operations to be preformed by the C.P.U.

Since the apparatus 80 does not have a blood flow sensor, only one gauge 84 is needed. The gauge 84 measures the chest compression force being applied to the patient. In the shown embodiment, the gauge 84 has two sets of identifying indicia. On one side of the gauge 84 is a numerical sequence 85 indicative of the actual pressure, in pounds per square inch, being applied. On the opposite side of the gauge 84 are multiple zones 86, 87, 88. Each zone may have an identifying indicia, such as "child" "small adult" and "average adult". The zones are disposed at positions that correspond to the proper pressure for a child, small adult and average adult respectively. As a result, the rescuer can see if he/she is applying the appropriate force to the patient.

It should be further understood that although the shown apparatus 80 utilizes a histogram-type gauge construction, that any other gauge may also be used. For example, the gauge could be a digital display, an analog dial gauge or any functionally equivalent gaging means.

The compression rate switch 82 shown has three settings, namely 60–80–100. However, it will be understood that additional settings or fewer settings may be used. In the simplified embodiment of FIG. 5, the internal C.P.U. can be greatly simplified. In the embodiment of FIG. 5, the visual indicators and audible indicator need only pace the rescuer. However, in the preferred embodiment, the chest compression force applied to a patient through is apparatus is detected by on electronic pressure sensor. Similarly, the gauge 84 is an electronically driven gauge that displays what is measured by the electronic pressure sensor. By eliminating the use of pneumatic or hydraulic gauges, the present invention device is more accurate, less expensive, lighter weight and more durable than other C.P.R. device currently available in the prior art.

It is understood that the embodiments described herein are merely exemplary and that a person skilled in the art may make variations and modifications to the described embodiments utilizing functionality equivalent components. All such variations and modifications are intended to within the spirit and the scope of the present invention as defined by the appended claims.

What is claimed is:

1. An apparatus for assisting in the application of cardiopulmonary resuscitation to a patient of a predetermined body type, comprising:

a housing capable of being placed on a patient's chest, said housing having at least one surface thereon adapted to receive a manually applied force;

a cushioned member extending from said housing, wherein said cushioned member contacts the patient's chest when said housing is placed on the patient and said manually applied force is applied to said housing;

an electronic force sensor coupled to said cushioned member, wherein said electronic force sensor produces a first sensor signal indicative of said manually applied force applied to said housing;

an electronic blood flow sensor coupled to said housing and attachable to the patient, wherein said blood flow sensor measures blood flow in the patient and produces a second sensor signal indicative of the blood flow;

a microprocessor contained within said housing, said microprocessor including a comparitor means for comparing said first sensor signal to a predetermined optimal compression force and comparing said second sensor signal to a predetermined optimal blood flow rate;

a warning means controlled by said microprocessor for providing a first warning alarm when said microprocessor determines that said second sensor signal is not within a predetermined range of said optimal blood flow rate;

a first display coupled to said housing for providing a visible display indicative of said first sensor signal; and a second display for providing a visible display indicative of said second sensor signal.

2. The apparatus according to claim 1, further including an indicator means for providing at least one indication to a person using the apparatus corresponding to a desired compressive rate per minute for the body type.

3. The apparatus according to claim 1, wherein said warning means provides a second warning alarm when said microprocessor determines that said first sensor signal is not within a predetermined range of said optimal compressive force.

4. The apparatus according to claim 2, wherein said at least one indication provided by said indicator means includes a periodic tone at said desired compressive rate wherein each tone corresponds in length to a predetermined compression stroke.

5. The apparatus according to claim 4, wherein said warning means provides a third warning alarm when the rescuer performs a compression stroke longer in duration than said predetermined compression stoke.

6. The apparatus according to claim 5, wherein said warning means provides a fourth warning alarm when the rescuer performs a compression stroke shorter in duration than said predetermined compression stroke.

7. The apparatus according to claim 2, wherein said warning means provides an indication when said manually applied force is not applied at said desired compressive rate per minute.

8. The apparatus according to claim 1, wherein said blood flow sensor includes a disposable ultrasonic transducer that is coupled to said housing by a wire tether that can be selectively detached from said housing when said blood flow sensor is disposed.

9. The apparatus according to claim 1, wherein said warning means includes a visual indicator for producing visible signals and an audible indicator for producing audible signals.

10. The apparatus according to claim 1, wherein said warning means includes a voice synthesizer for generating a synthesized spoken command.

11. The apparatus according to claim 2, wherein said microprocessor includes a counting means therein for counting the number of times said manually applied force is applied to said housing and said indicator means produces an instruction signal indicative of when mouth-to-mouth resuscitation should administered in relation to the number of times said manually applied force is applied.

12. The apparatus according to claim 1, wherein said first display and said second display are both part of an electronic display disposed on said housing.

13. The apparatus according to claim 12, further including a selecting means disposed on said housing, for selecting the body type of the patient.

14. The apparatus according to claim 13, wherein said microprocessor includes a means for scaling said first display and said second display depending on the patient's physical body type selected.

\* \* \* \* \*